United States Patent [19]
Klein

[11] Patent Number: 5,957,874
[45] Date of Patent: Sep. 28, 1999

[54] HEEL ELEVATING DEVICE

[75] Inventor: Stephen J. Klein, Cordova, Tenn.

[73] Assignee: Tharos LLC, Cordova, Tenn.

[21] Appl. No.: 09/008,046

[22] Filed: Jan. 16, 1998

[51] Int. Cl.[6] .................................................. A61F 5/00
[52] U.S. Cl. .............................. 602/23; 602/28; 5/650; 128/882
[58] Field of Search .................................. 602/60–65, 5, 602/23, 27–29, 12, 15; 128/846, 877, 882; 607/111, 112; 5/648, 650, 651; 264/222, DIG. 30

[56] References Cited

U.S. PATENT DOCUMENTS

| | | |
|---|---|---|
| D. 388,995 | 1/1998 | Hargest et al. . |
| 3,008,464 | 11/1961 | Atkins .......................... 128/DIG. 23 X |
| 4,104,746 | 8/1978 | Goetz . |
| 4,186,738 | 2/1980 | Schleicher et al. . |
| 4,197,845 | 4/1980 | Browning . |
| 4,266,298 | 5/1981 | Graziano . |
| 4,350,726 | 9/1982 | Berry, Jr. .................................. 428/95 |
| 4,399,815 | 8/1983 | Bachorik . |
| 4,472,838 | 9/1984 | Pompa ......................................... 2/460 |
| 4,478,214 | 10/1984 | Lamont . |
| 4,573,456 | 3/1986 | Spann . |
| 4,941,480 | 7/1990 | McLean et al. ........................ 128/878 |
| 5,085,214 | 2/1992 | Barrett . |
| 5,367,789 | 11/1994 | Lamont . |
| 5,449,339 | 9/1995 | Drennan . |
| 5,609,570 | 3/1997 | Lamont . |
| 5,716,334 | 2/1998 | Wade . |
| 5,725,486 | 3/1998 | Engelman .................................... 602/5 |

*Primary Examiner*—Richard J. Apley
*Assistant Examiner*—Denise Pothier
*Attorney, Agent, or Firm*—Adams Law Firm, P.A.

[57] ABSTRACT

A heel elevating device is adapted for being applied to the lower leg of a reclined patient to elevate the heel of the patient above a supporting surface. The heel elevating device includes a generally U-shaped lower leg support having a base and first and second opposed extensions. The extensions define an opening therebetween for receiving and supporting the lower leg of the patient. A comfort liner is secured to an interior of the lower leg support for cushioning the lower leg and providing a soft, protective surface against the skin of the patient. Adjustable fitting straps are provided for adjustably fitting the lower leg support to the lower leg of the patient.

18 Claims, 7 Drawing Sheets

HEEL ELEVATING DEVICE

TECHNICAL FIELD AND BACKGROUND OF THE INVENTION

This invention relates to a heel elevating device. The invention elevates the foot of a patient who is in a reclined position, and who is beginning to experience skin breakdown or has developed a pressure sore or pressure ulcer, venous ulcer, or diabetic ulcer on a portion of the foot, especially the heel. By elevating the foot and preventing it from contacting the bed sheets or other surface, further incidence of skin damage is reduced. Skin tissue which is already damaged heals faster because it does not come into contact with any type of hard surface, and air is allowed to circulate around it. Air circulation is essential to healing pressure sores, pressure ulcers, venous ulcers, or diabetic ulcers.

In addition, the invention is applicable for hospital, rehabilitation center, nursing home and home care patients who are bedridden or spend a considerable amount of time in bed. These patients are highly susceptible to developing pressure sores and pressure ulcers on a portion of the foot, especially the heel. It is also applicable for persons with diabetes who are very susceptible to diabetic foot ulcers caused by poor circulation, and non-diabetic persons with poor circulation who are susceptible to venus ulcers.

The present invention is further applicable in passive stretch therapy for persons having recently undergone knee surgery, or having suffered some type of knee injury. "Passive stretch" is a procedure for regaining total extension of the knee. The procedure involves placing a weighted bag on the knee of a patient in a reclined or sitting position on a bed or therapy table. The weight causes the knee to extend. Treatments lasts approximatetly 15 to 20 minutes each, and are repeated over several days or weeks until the patient has attained total extension of the knee.

The invention is placed under the patient's ankle and maintains the foot, ankle, knee and leg in a generally fixed position, preventing the weight placed on the knee from shifting during treatment. The U-shaped design of the invention, and inner liner, adjustable top strap, and adjustable foot-drop strap secure the foot and ankle in an upright position, while maintaining a high level of comfort for the patient. In addition, the invention raises the ankle and foot which in turn aids in the knee extension process. Patients who cannot be placed in a knee brace because they are tissue compromised (at high risk of developing pressure sores and/or ulcers caused by skin contact with the knee brace) can also be helped by using this invention during passive stretch for knee extension therapy.

The invention is especially applicable for use by the following types of persons:

a. Hospitalized patients who have come out of surgery with heel shear (heel has rubbed on the operating room table during the surgical procedure).

b. Hospital, rehabilitation center, nursing home and home care patients who are bedridden or spend a considerable amount of time in bed. These patients are highly susceptible to developing skin shear, pressure sores and pressure ulcers on any portion of the foot, especially the heel.

c. Persons with diabetes who have diabetic foot ulcers caused by this disease.

d. Persons with poor circulation who develop venous ulcers as a result circulatory impairment.

e. Hospital and independent rehabilitation center in-patients and out-patients who are undergoing passive stretch for knee extension therapy as a result of orthopedic knee surgery or a knee injury.

There are a number of heel protectors and heel elevators in the prior art, but none of which adequately satisfy the needs of patients and care-givers as compared to the present invention. These products are divided into the following general categories based on estimated cost of the product:

Relatively Low Price Heel Protectors ($6 to $12 range)

These type products generally cover the bottom and sides of the foot and attach across the top of the foot with VELCRO™ hook and loop straps. They are usually made of open-cell foam or a cotton pad sewn into a nylon cover, and is designed to cushion the foot from contact with bed sheets or any hard surface. These products do not work satisfactorily for patients who already have skin shear, chaffing, pressure sores, pressure ulcers, venous ulcers or diabetic ulcers.

Some primary disadvantages are that these products apply pressure to the affected area or areas on the heel and/or foot causing pain and further skin damage. Even though these products are made of a very soft material, constant contact of this material with irritated or compromised skin tissue can create new sores or ulcers. Moreover, skin tissue can be torn or damaged when the device is removed because the material of this device may stick to the skin or wound. These products block air circulation necessary for healing and for patient comfort, and do nothing to help prevent "foot-drop", a condition that often results from trauma or paralysis of the muscles which flex the foot. This condition results from failure to maintain the foot in a normal 90° fixed position, and can cause dragging of the foot.

Relatively Low Price Heel Elevators ($12 to $25 range)

These type products generally include open-cell foam circles or blocks with a cut-out hole for the ankle. Some have a permanently attached or removable adjustable foot-drop strap and an adjustable top strap, but no cushion liner. The type of open-cell foam used in these products often collapses, forming a rigid surface area which in turn can cause skin irritation, skin shear, chaffing, pressure sores or pressure ulcers. When the product collapses under the weight of the patient's calf, ankle and foot, the heel and foot end up resting on the bed sheets or other relatively hard surface areas. Since the hole for the ankle is pre-cut and cannot be adjusted, it can be too tight for some patients and too loose for others.

In addition, most of these type products do not have a foot-drop strap, and none of them can be machine washed for re-use. The foam base without a padded liner provides an extremely hard and abrasive surface for the ankle which can cause ankle pressure sores or pressure ulcers. Furthermore, these products generally do not remain in the proper position when the patient flexes his/her knee or turns from side to side.

Mid-Price Heel Elevators ($25 to $40 range)

Two commercially-available, inflatable products in this category include THE HEELER™ and WAFFLE BOOT™. THE HEELER™ has a thin removable shearling liner, and the WAFFLE BOOT™ has a thin synthetic cloth type liner. Both liners must be removed for laundering because the vinyl inflatable bases cannot withstand machine washing and drying. Liners are often misplaced or lost and replacements must be purchased. The vinyl base of both products can be over inflated creating excessive pressure at the point of contact with the ankle and Achilles tendon which can result in skin breakdown in these areas. The base can also be under inflated causing the heel and Achilles tendon area to come into contact with bed sheets or other relatively hard surface areas. The base can also be easily punctured making the product no longer usable.

The WAFFLE BOOT™ has a built-in foot-drop strap which helps to prevent foot-drop, and keep the product in the proper position when the patient moves or turns from side to side. The HEELER™ does not have a foot-drop strap, and frequently will not remain in the proper position if the patient flexes his/her knee or turns from side to side. The product of the present invention falls in this category.

Relatively High Price Heel Elevators ($175–$200 range)

One commercially-available product in this category is sold under the trademark MULTTPODUS BOOT™. This product is a half-boot design that is open on the top half and extends from the top of the calf to the bottom of the ankle. The product is formed of a hard plastic outer shell with a thin shearling liner, and a series of VELCRO™ straps that secure the product to the calf and ankle. A metal bracket extends from the bottom of the boot, loops out at the heel, and loops back to the bottom of the foot keeping the heel off hard surfaces. The MULNPODUS BOOT™ keeps the heel elevated, helps prevent foot-drop, and remains in position when the patient flexes his/her knee or turns from side to side. Also, patients can walk while wearing this product, and can wear the product in bed.

Unlike the present invention, the MULTTPODUS BOOT™ is very expensive and cannot be machine washed as a unit. This product is also restrictive because of its hard plastic outer shell which can create pressure on the calf and ankle causing pressure sores and pressure ulcers. The metal bracket sometimes rubs against the bottom of the foot creating a pressure sore or pressure ulcer in this area. Moreover, it takes more time to affix and remove this product from the patient than other types of heel elevator devices.

SUMMARY OF THE INVENTION

Therefore, it is an object of the invention to provide a heel elevating device which functions as a system to help reduce the incidence of chaffing, skin shear, pressure sores or pressure ulcers, venous ulcers, or diabetic ulcers.

It is another object of the invention to provide a heel elevating device which promotes air circulation around the ankle.

It is another object of the invention to provide a heel elevating device which is easy to apply to and remove from the lower leg of the patient without sliding the device across the Achilles tendon and heel, or over the top of the foot. Sliding any soft material across a sore or ulcer can be painful for the patient and may cause further skin damage.

It is another object of the invention to provide a heel elevating device which cushions and protects the ankle and Achilles tendon area of the patient regardless of his/her position—whether lying on the back, right side or left side.

It is another object of the invention to provide a heel elevating device which properly maintains the foot of the patient off the supporting surface regardless of his/her position—whether lying on the back, right side or left side.

It is another object of the invention to provide a heel elevating device including a cushion bladder with a thermal gel or liquid which can be warmed in a microwave oven to enhance blood flow to the foot. Alternatively, the device may include a contoured foam cushion insert instead of a bladder.

It is another object of the invention to provide a heel elevating device which can be machine washed and tumbled or drip dried as one complete unit.

It is another object of the invention to provide a heel elevating device which does not include separate parts which can be misplaced or lost.

It is another object of the invention to provide a heel elevating device which permits continuous visual inspection of the foot or foot wound site.

It is another object of the invention to provide a heel elevating device which does not need to be removed in order to clean or treat a wound and/or change wound dressings.

It is another object of the invention to provide a heel elevating device which has a slick outer surface finish for allowing the device to slide on bed sheets or any hard surface.

It is another object of the invention to provide a heel elevating device which remains in its proper secured position on the lower leg when the patient moves or is turned from side to side.

It is another object of the invention to provide a heel elevating device which includes a rough textured outer surface finish to restrict sliding of the foot over the supporting surface.

It is another object of the invention to provide a heel elevating device which allows no movement of the foot from side to side for patients whose foot must remain stationary.

It is another object of the invention to provide a heel elevating device which permits limited movement of the foot from side to side for those patients who are allowed some limited foot movement.

It is another object of the invention to provide a heel elevating device which significantly reduces pressure to the ankle and lower leg by evenly dispersing the pressure, even when in place for long periods of time.

It is another object of the invention to provide a heel elevating device which is comfortable for the patient.

It is another object of the invention to provide a heel elevating device which does not restrict blood flow to, or air circulation around, the foot of the patient.

It is another object of the invention to provide a heel elevating device which promotes blood circulation to the foot.

It is another object of the invention to provide a heel elevating device which adjusts to fit a wide range of sizes.

It is another object of the invention to provide a heel elevating device which helps prevent a malady known as "foot-drop".

It is another object of the invention to provide a heel elevating device which minimizes friction and evenly disperses pressure at the point of contact on the ankle and Achilles tendon area, thereby reducing the possibility of skin shear, chaffing or pressure sores to these areas.

These and other objects of the present invention are achieved in the preferred embodiments disclosed below by providing a heel elevating device for being applied to the lower leg of a reclined patient to elevate the heel of the patient above a supporting surface. The heel elevating device includes a generally U-shaped lower leg support having a base and first and second opposed extensions. The extensions define an opening therebetween for receiving and supporting the lower leg of the patient. A comfort liner is secured to an interior of the lower leg support for cushioning the lower leg and providing a soft, protective surface against the skin of the patient. Adjustable fitting means are provided for adjustably fitting the lower leg support to the lower leg of the patient.

According to one preferred embodiment of the invention, the adjustable fitting means includes an adjustable top strap adapted for extending over a top of the extensions, and for adjustably spacing the extensions to snugly embrace the lower leg. The top strap has a connecting end attached to the first extension of the lower leg support, and a free end for being removably attached to the second extension of the lower leg support.

According to another preferred embodiment of the invention, the free end of the top strap and the second extension of the lower leg support include complementary hook and loop attachment members for removably attaching the top strap to the second extension.

According to yet another preferred embodiment of the invention, an inside surface of the top strap includes shearling for providing a soft, protective surface against the skin of the patient.

According to yet another preferred embodiment of the invention, the adjustable fitting means includes an adjustable foot-drop strap adapted for extending around the bottom of the foot to raise and maintain the foot in a generally 90° position. The foot-drop strap includes a connecting end attached to the first extension of the lower leg support, and a free end for being removably attached to the second extension of the lower leg support.

The term "adjustable fitting means" includes means for adjusting the spacing between the extensions by adjustment of the top strap, and for adjusting the support to the bottom of the foot by adjustment of the foot-drop strap.

According to yet another preferred embodiment of the invention, an inside surface of the foot-drop strap includes shearling for providing a soft, protective surface against the skin of the patient.

According to yet another preferred embodiment of the invention, the comfort liner includes shearling.

According to yet another preferred embodiment of the invention, the comfort liner includes a gel-filled thermal bladder.

According to yet another preferred embodiment of the invention, the comfort liner includes a contoured foam insert.

According to yet another preferred embodiment of the invention, the comfort liner includes an air bladder.

According to yet another preferred embodiment of the invention, a bottom surface of the comfort liner and a top surface of the base of the lower leg support include respective complementary hook and loop attachment members for removably attaching the comfort liner to the base of the lower leg support.

According to yet another preferred embodiment of the invention, a bottom surface of the comfort liner and an inside surface of each of the first and second extensions of the lower leg support include respective complementary hook and loop attachment members for removably attaching the comfort liner to the first and second extensions of the lower leg support.

According to yet another preferred embodiment of the invention, the lower leg support is formed of a semi-rigid, resilient foam material.

According to yet another preferred embodiment of the invention, the base and first and second extensions of the lower leg support are integrally-formed.

According to yet another preferred embodiment of the invention, the base of the lower leg support has a slick bottom surface for allowing sliding movement of the lower leg support over the supporting surface.

According to yet another preferred embodiment of the invention, the base of the lower leg support has a textured bottom surface for restricting sliding movement of the lower leg support over the supporting surface.

According to yet another preferred embodiment of the invention, the base of the lower leg support has a flat bottom surface for maintaining the foot in stationary position.

According to yet another preferred embodiment of the invention, the base of the lower leg support includes a rounded bottom surface for allowing limited side to side movement of the foot.

According to yet another preferred embodiment of the invention, the first and second extensions of the lower leg support have generally flat, respective outer surfaces.

BRIEF DESCRIPTION OF THE DRAWINGS

Some of the objects of the invention have been set forth above. Other objects and advantages of the invention will appear as the description proceeds when taken in conjunction with the following drawings, in which.

DESCRIPTION OF THE PREFERRED EMBODIMENT AND BEST MODE

Figure 1:
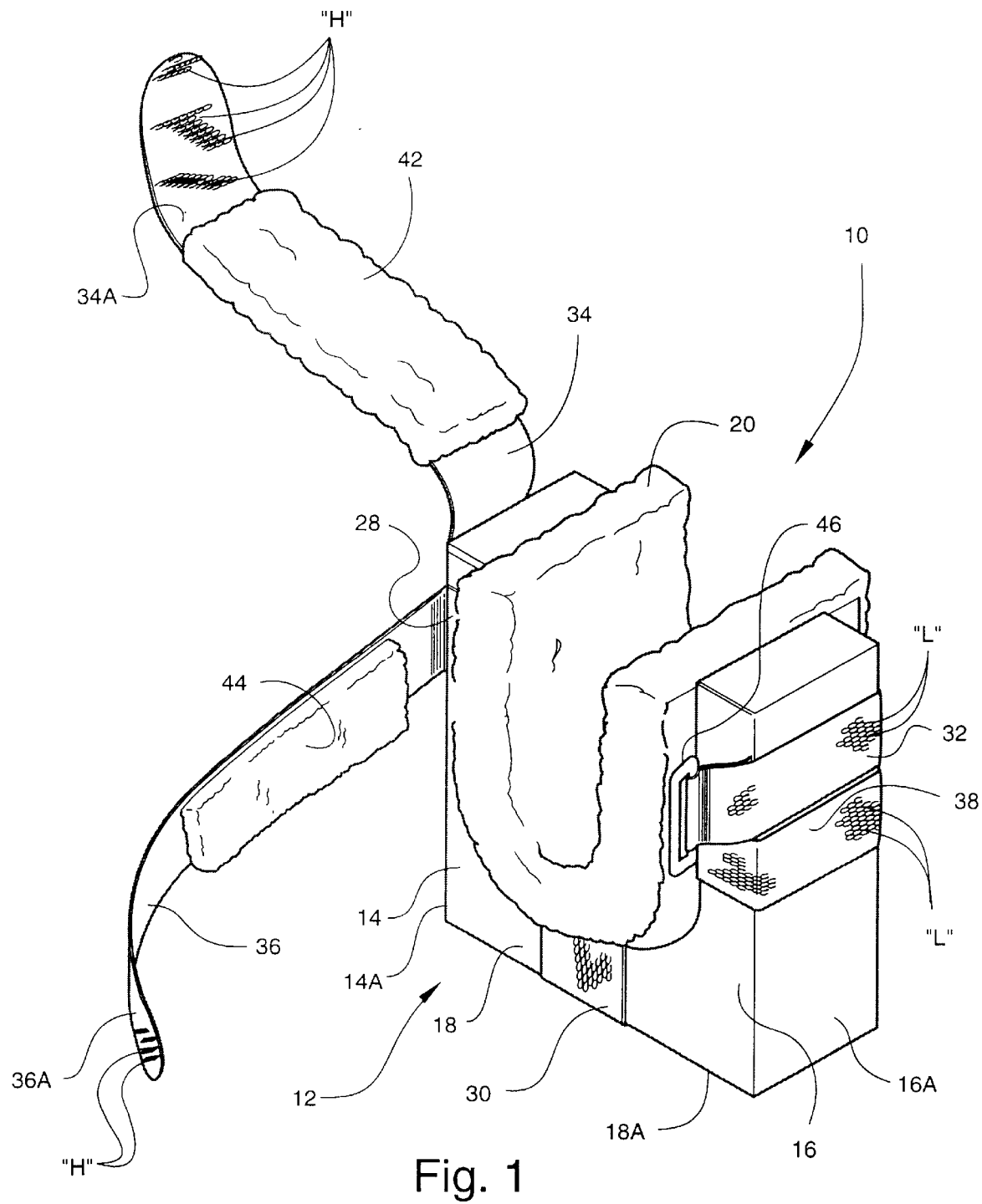
FIG. 1 is a perspective view of a heel elevating device according to one preferred embodiment of the invention, and showing the fitting straps detached prior to application of the device to the lower leg of the patient.

Referring now specifically to the drawings, a heel elevating device according to the present invention is illustrated in FIG. 1 and shown generally at reference numeral 10. The heel elevating device 10 is especially applicable for supporting the lower leg of a reclined patient above a hard surface, such as a bed mattress. Even light contact between the heel and mattress or bed sheets, for example, can aggravate skin aliments such as chaffing, skin shear, pressure sores, pressure ulcers, venous ulcers, and diabetic ulcers. The heel elevating device 10 further promotes fast healing of damaged skin tissue by allowing air circulation around the affected area of foot.

Figure 2:
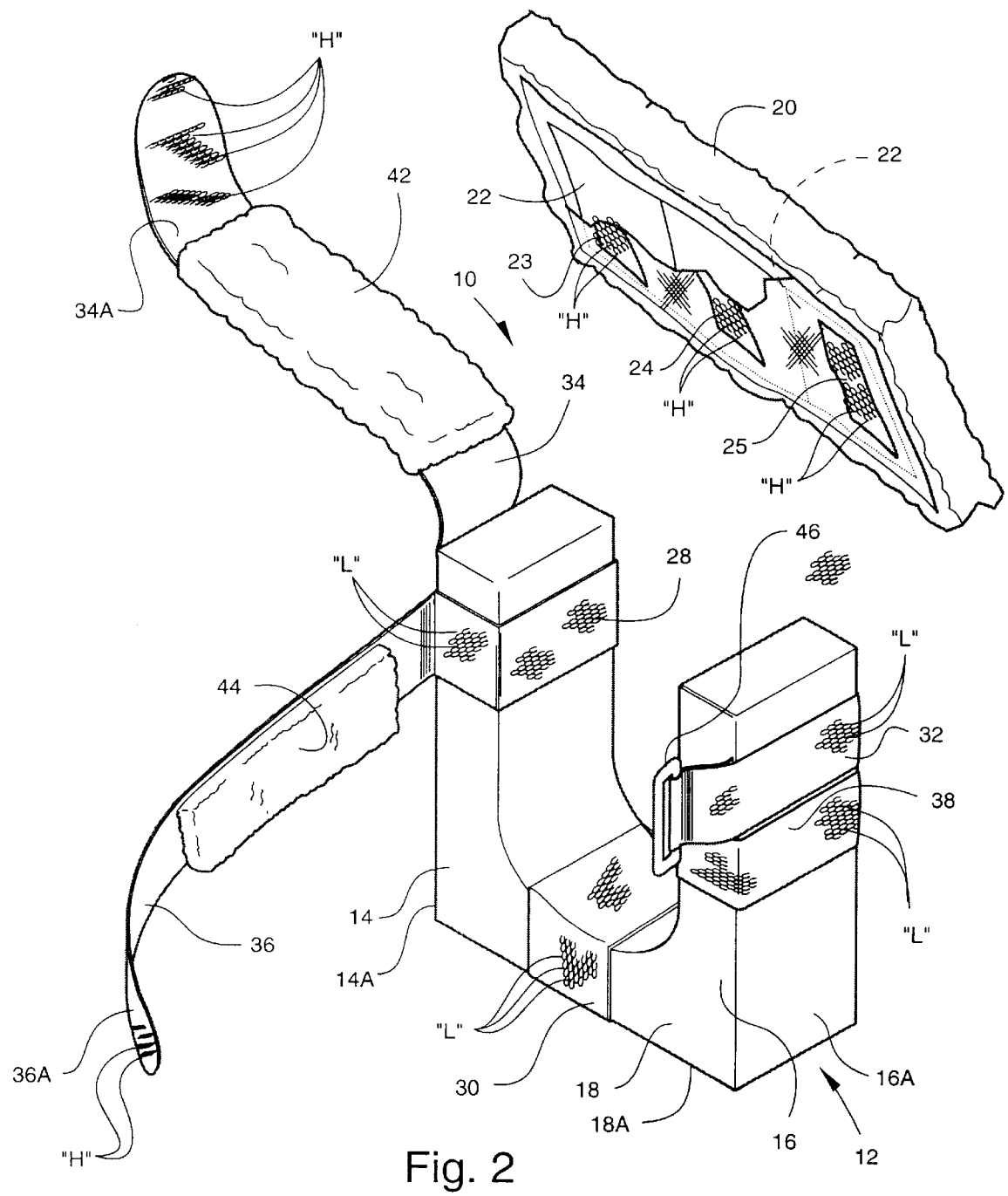
FIG. 2 is a perspective view of the heel elevating device with the shearling comfort liner removed, and showing a portion of the comfort liner broken away to expose the gel bladder.

Referring to FIGS. 1 and 2, the heel elevating device 10 includes a selfstanding, generally U-shaped, lower leg support 12 having first and second spaced extensions 14 and 16 and a base 18. The term "U-shaped" is defined broadly herein as a shape having an open central area with opposed, upward extending walls on either side. For example, the term includes, but is not limited to, those shapes which are generally V-shaped or horseshoe-shaped. The extensions 14 and 16 and base 18 are preferably integrally formed together of a resilient, semi-rigid, open-cell or closed-cell foam material. Alternatively, the lower leg support 12 may be formed of an upright, air or liquid filled member capable of supporting the weight of the patient's lower leg without collapsing.

A removable, shearling comfort liner 20 is secured to the interior of the lower leg support 12 to cushion the lower leg of the patient and protect the ankle and Achilles tendon area against skin shear, chaffing, or other skin breakdown. The comfort liner 20 preferably includes a sewn-in, multi-compartment bladder 22 filled with a thermal liquid gel. The shearling and bladder cooperate to evenly distribute pressure on the lower leg, and to provide maximum comfort to the patient when using the device 10 over a long period of time. The shearling and bladder also cooperate to prevent skin breakdown. In addition, the liner 20 can be placed in a microwave oven to heat the gel-filled bladder 22 prior to application of the device 10 to the lower leg. The heated liner 20 further promotes blood flow and circulation to the foot. According to an alternative embodiment, the bladder is filled with other liquid or air.

As shown in FIG. 2, the comfort liner 20 is removably attached to interior walls of the lower leg support 12 by mating complementary hook strips 23, 24 and 25, and loop strips 28, 30, and 32 located, respectively, on the bottom surface of the liner 20 and on the top surface of the base 18 and inside surface of each extension 14 and 16. The loop strips 28, 30, and 32 preferably extend entirely around the base 18 and extensions 14 and 16, respectively. Should the liner 20 become worn or require washing, it can be readily removed and replaced with a fresh liner.

Figure 3:
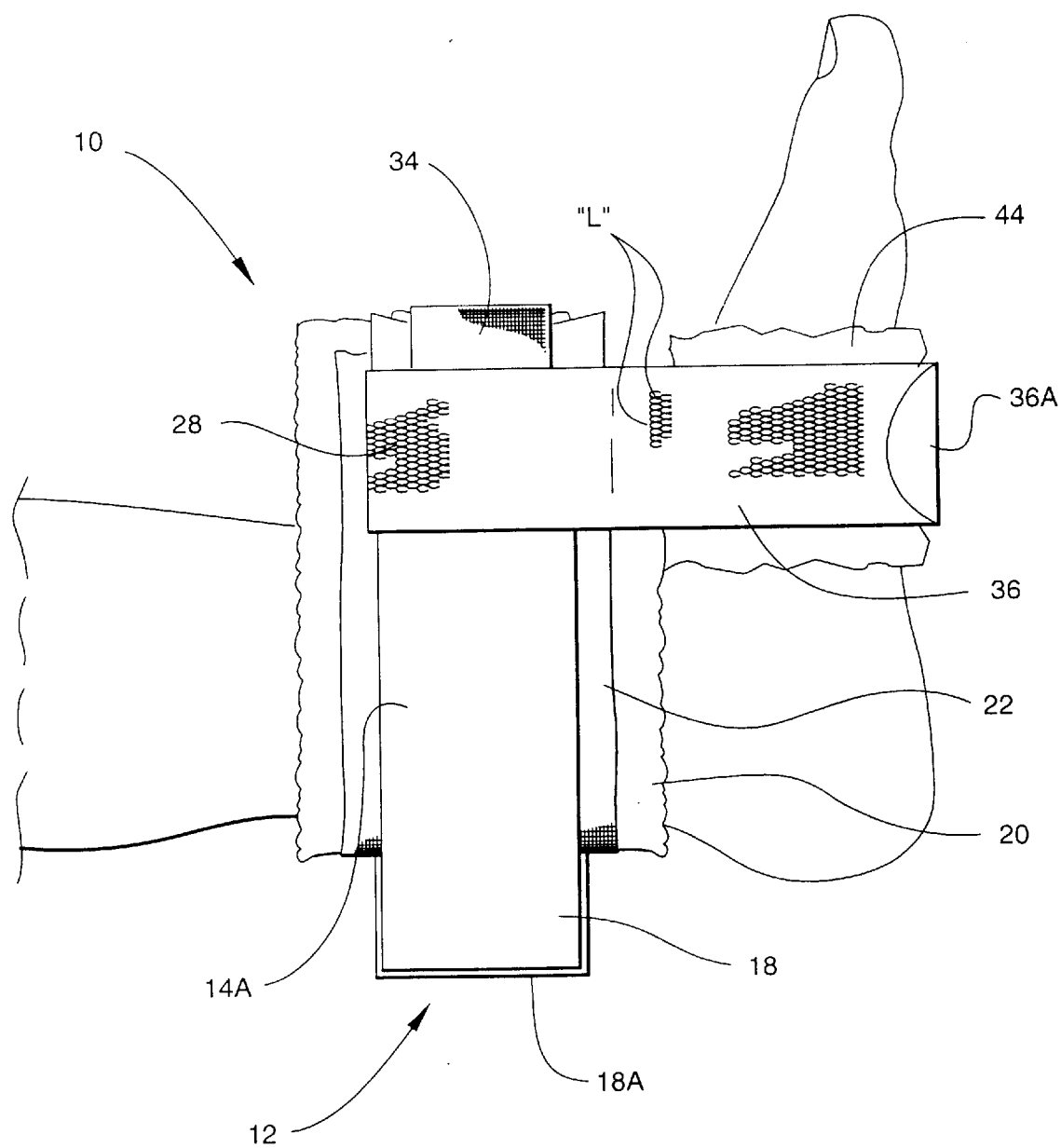
FIG. 3 is a side elevational view of the heel elevating device as applied to the lower leg of the patient.
Figure 4:
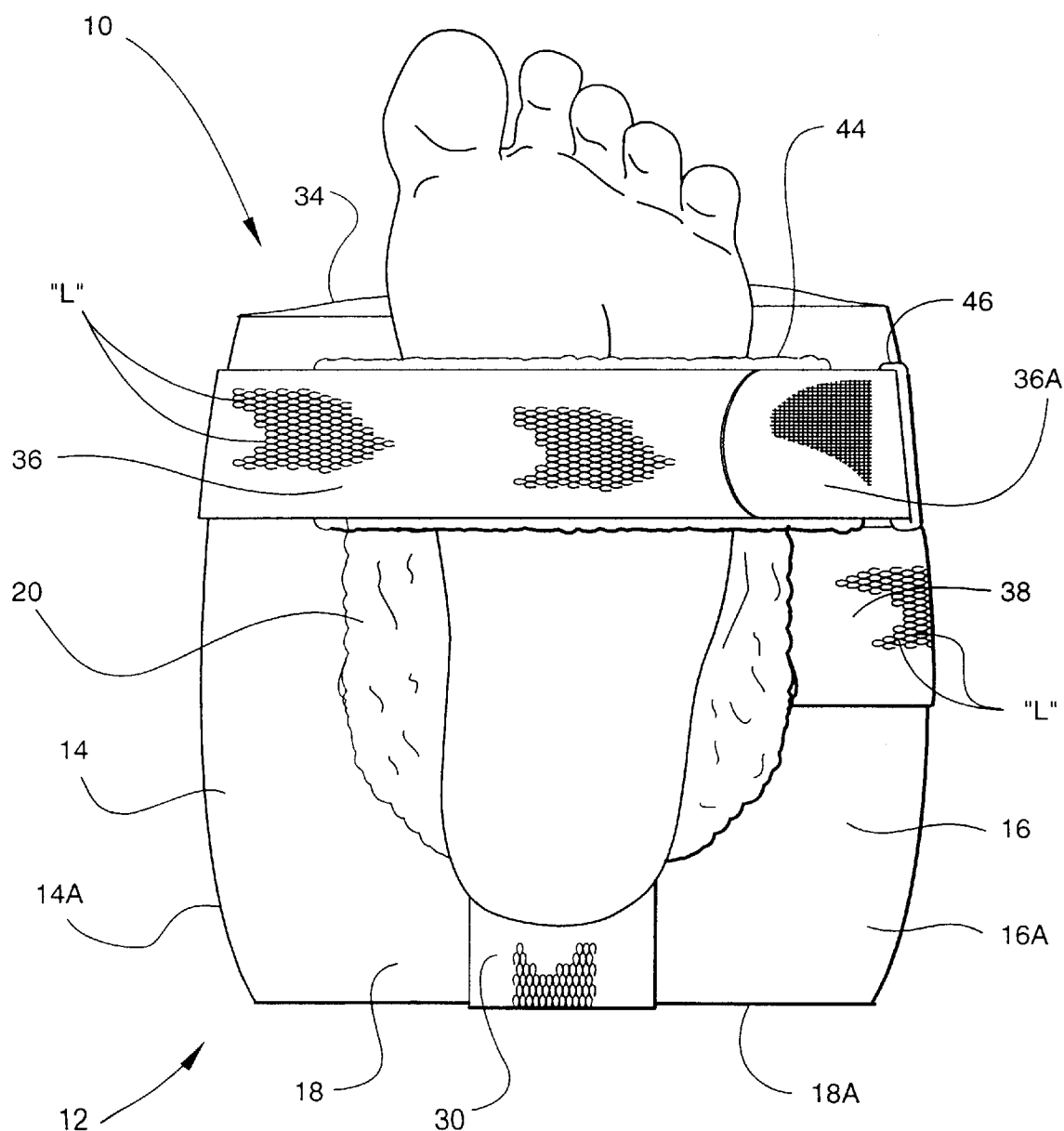
FIG. 4 is a front elevational view of the heel elevating device as applied to the lower leg of the patient.
Figure 5:
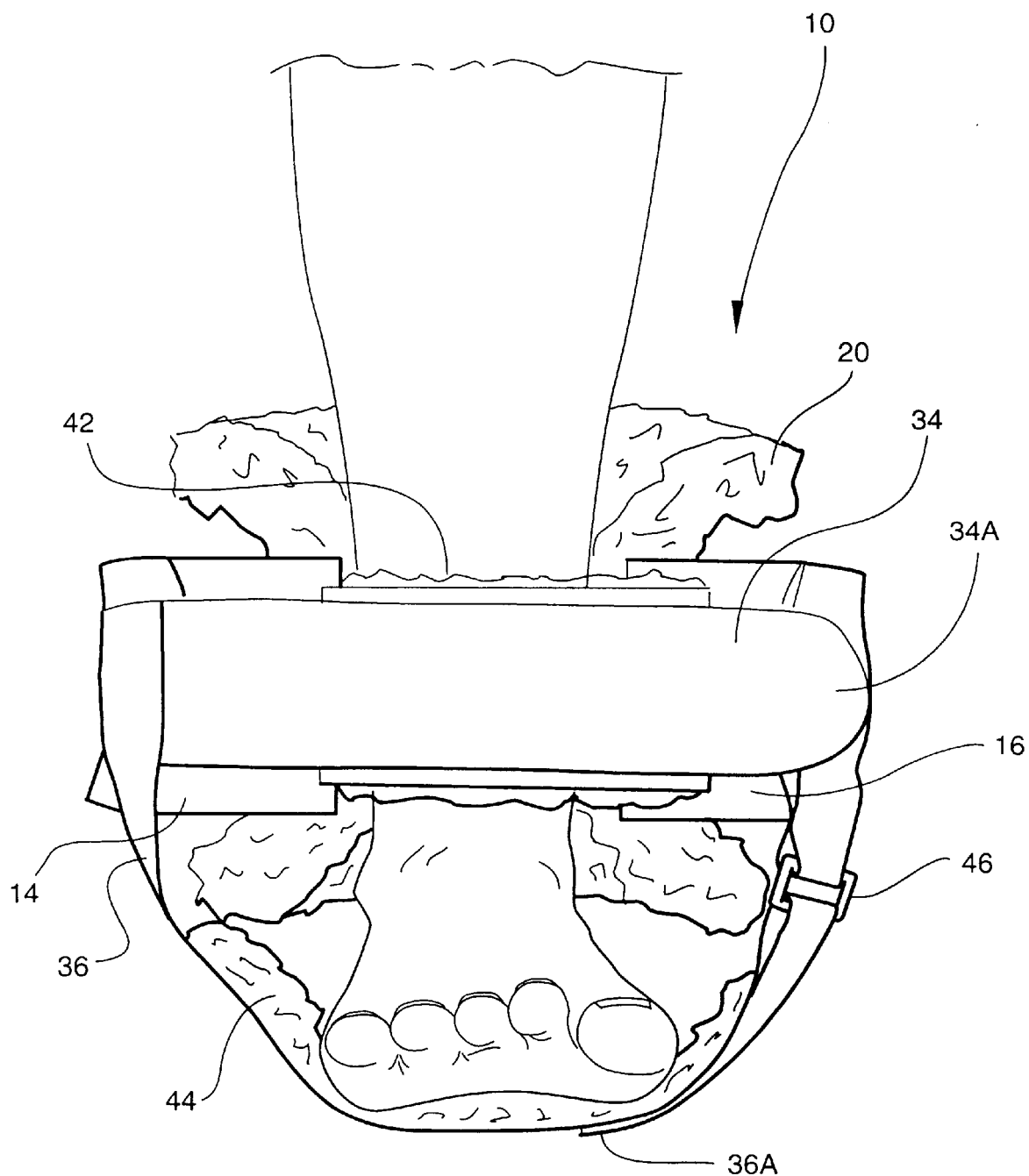
FIG. 5 is a top plan view of the heel elevating device as applied to the lower leg of the patient.

FIGS. 3, 4, and 5 illustrate the heel elevating device 10 as applied to the lower leg of the patient. As shown, the lower leg support 12 is properly fitted to the patient using an adjustable top strap 34 attached to the extension 14 and adapted for extending over the lower leg, and an adjustable foot-drop strap 36 attached to the extension 14 and extending across the ball of the foot. The foot-drop strap 36 guards against a malady known as "foot-drop" by raising and maintaining the foot in a generally upright, slightly flexed 90° position.

The free end 34A of the top strap 34 includes hook members "H" adapted for mating with complementary loop members "L" formed on the loop strip 32 and an adjacent loop strip 38 secured to the extension 16. Preferably, the top strap 34 includes shearling 42 which cushions the strap 34 against the skin of the patient. The foot-drop strap 36 likewise includes shearling 44, and hook members "H" formed on a back side of its free end 36A. The free end 36A of the foot-drop strap 36 extends through a catch 46, and folds over onto itself to mate with complementary loop members "L" (See FIG. 4) formed on the strap 36 adjacent the hook members "H". The adjustable top strap 34 and foot-drop strap 36 cooperate to maintain proper placement of the device 10 on the lower leg of the patient, even when the patient is turned.

According to the embodiment of FIGS. 1–5, the bottom surface 18A of the base 18 is substantially flat for restricting side-to-side movement of the patient's foot, and may have a slick finish for allowing the lower leg support 12 to slide over the bed mattress or other supporting surface during use. Alternatively, the bottom surface 18A has a nonslick or rough-textured finish which limits sliding of the lower leg support 12. The outside surface 14A, 16A of each extension 14, 16 is also generally flat to restrict movement of the foot when the patient is lying on his/her side.

Figure 6:
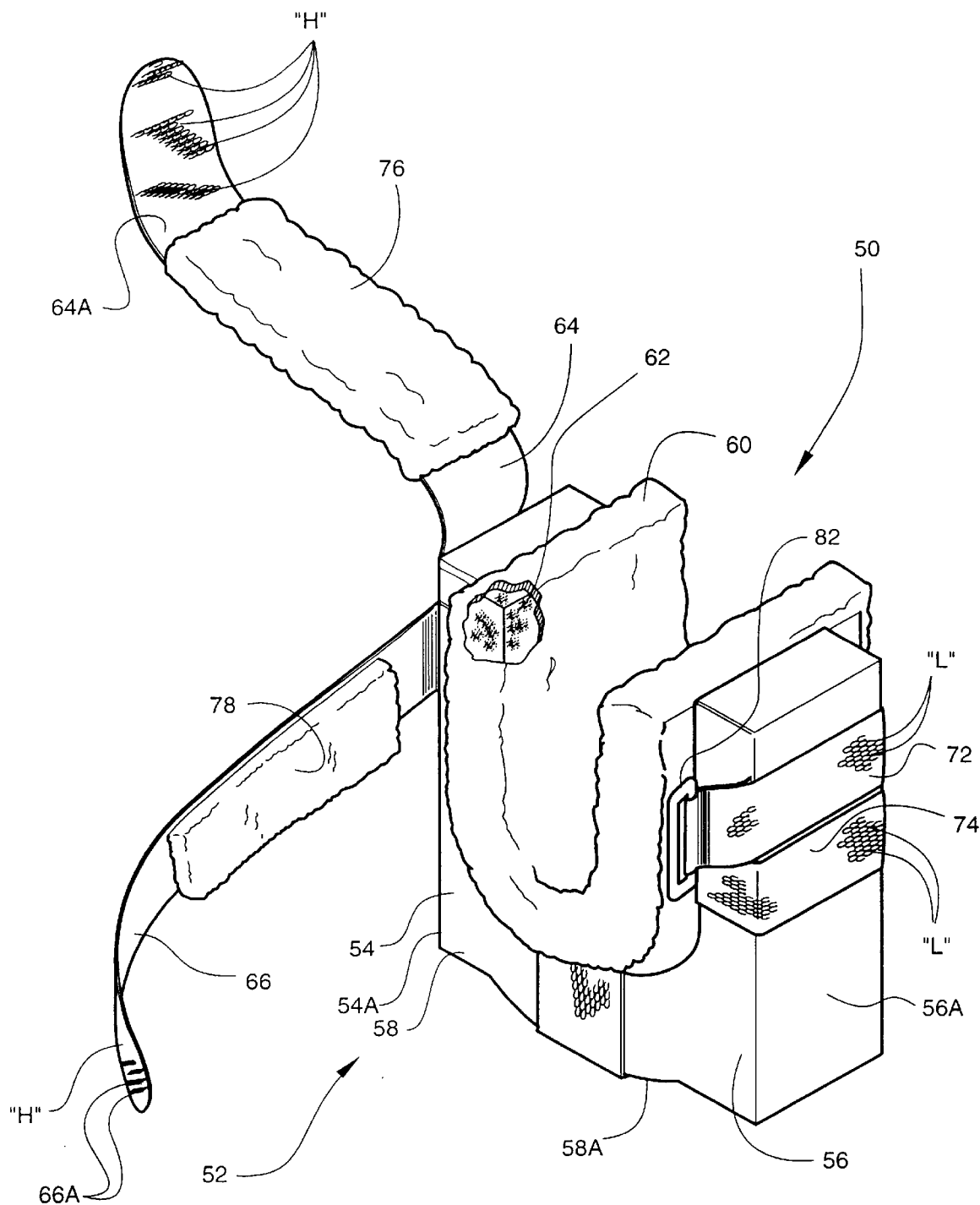
FIG. 6 is a perspective view of the heel elevating according to a second preferred embodiment of the invention, and showing a portion of the comfort liner broken away to expose the foam cushion insert.

An alternative embodiment of a heel elevating device 50 according to the present invention is shown in FIG. 6. The heel elevating device 50 includes a self-supporting generally U-shaped, lower leg support 52 having first and second opposed extensions 54 and 56 and a base 58. A removable, shearling comfort liner 60 is secured to interior walls of the lower leg support 52 to cushion the lower leg of the patient and protect the ankle and Achilles tendon area against skin shear, chaffing, or other skin breakdown. The comfort liner 60 includes a contoured foam insert 62.

The lower leg support 52 is properly fitted to the patient using an adjustable top strap 64 attached to the extension 54 and adapted for extending over the lower leg, and an adjustable foot-drop strap 66 attached to the extension 54 and extending across the ball of the foot to raise and maintain the foot in a 900 position. The free end 64A of the top strap 64 includes hook members "H" adapted for mating with complementary loop members "L" formed on adjacent loop strips 72 and 74 secured around the extension 56. Preferably, the top strap 64 includes shearling 76 for cushioning the strap 64 against the skin of the patient. The foot-drop strap 66 likewise includes shearling 78, and hook members "H" formed on a back side of its free end 66A. The free end 66A of the foot-drop strap 66 extends through a catch 82, and folds over onto itself to mate with complementary loop members (not shown) formed on the strap 66 adjacent the hook members "H".

According to the embodiment of FIG. 6, the bottom surface 58A of the base 58 is rounded for allowing a limited range of side-to-side movement of the patient's foot. The rounded portion may be separately attached to the base 58 using a suitable adhesive, or may be integrally formed with the base 58. In addition, the bottom surface 58A may have a slick finish for allowing the lower leg support 52 to slide over the bed mattress or other supporting surface. Alternatively, the bottom surface 58A has a non-slick or rough-textured finish which limits sliding of the lower leg support 52. The outside surface 54A, 56A of each extension 54, 56 is generally flat to restrict movement of the foot when the patient is lying on his/her side.

Figure 7:
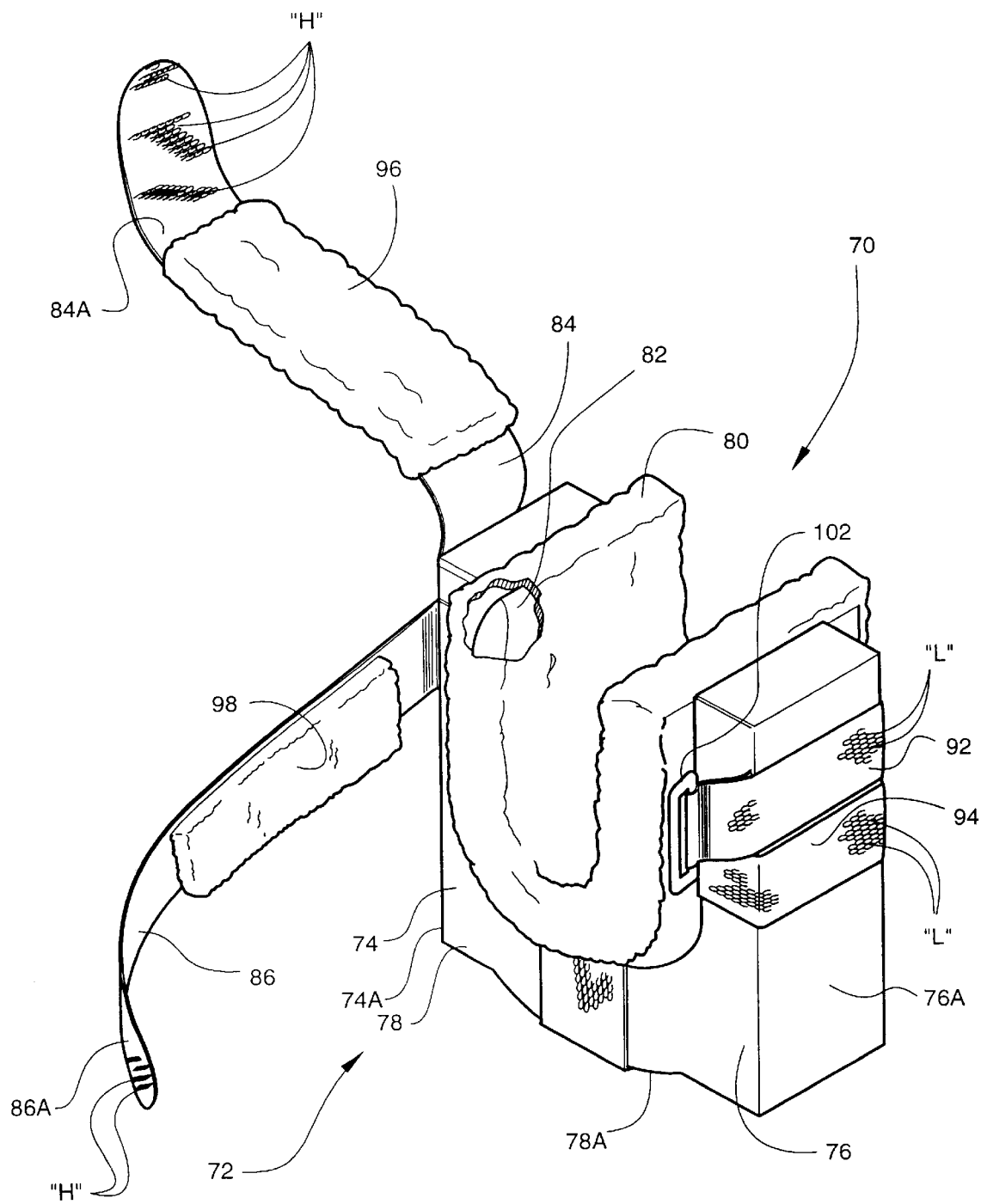
FIG. 7 is a perspective view of the heel elevating device according to a third preferred embodiment of the invention, and showing a portion of the comfort liner broken away to expose the air bladder.

A further embodiment of invention is shown in FIG. 7. Like the devices previously described, the heel elevating device 70 includes a self-supporting, generally U-shaped, lower leg support 72 having first and second opposed extensions 74 and 76 and a base 78. A removable, shearling comfort liner 80 is secured to the interior of the lower leg support 72 to cushion the lower leg of the patient and protect the ankle and Achilles tendon area against skin shear, chaffing, or other skin breakdown. The comfort liner 80 includes a sewn-in, inflatable air bladder 82.

The lower leg support 72 is properly fitted to the patient using an adjustable top strap 84 attached to the extension 74 and adapted for extending over the lower leg, and an adjustable foot-drop strap 86 attached to the extension 74 and extending around the ball of the foot to raise and maintain the foot in a 90° position. The free end 84A of the top strap 84 includes hook members "H" adapted for mating with complementary loop members "L" formed on adjacent loop strips 92 and 94 secured around the extension 76. Preferably, the top strap 84 includes shearling 96 for cushioning the strap 84 against the skin of the patient. The foot-drop strap 86 likewise includes shearling 98, and hook members "H" formed on a back side of its free end 86A. The free end 86A of the foot-drop strap 86 extends through a catch 102, and folds over onto itself to mate with complementary loop members (not shown) formed on the strap 86 adjacent the hook members "H". The bottom surface 78A of the base 78 is rounded for allowing a limited range of side-to-side movement of the patient's foot. The outside surface 74A, 76A of each extension 74, 76 is generally flat to restrict movement of the foot when the patient is lying on his/her side.

An exemplary product specification for a heel elevating device made in accordance with one preferred embodiment of the present invention follows:

Lower Leg Support

| | |
|---|---|
| Material: | one piece, cross-linked polyethylene, mini-cell type LF and MS; |
| Weight: | 3 ounces; |
| Finish: | Slick on outside edges of base and edges of extensions; |
| Dimensions: | 3" depth; 7½" width; 8" length from top of extensions to bottom of base; and 1¼" length from center of lower leg support to bottom of base. |

Shearling Comfort Liner

| | |
|---|---|
| Face Material: | 90% polyester and 10% acrylic, pile about ½"–1"; and |
| Dimensions: | 5¾" width, 16" length (unfolded). |

Thermal Liquid Gel Bladder

| | |
|---|---|
| Material: | 89.77% water, 10.11% propylene glycol, .102% azoniasdamiane chloride, .023% benzene, and .004% ethanol sealed in a three-compartment, two layer bag; |
| Weight: | 14 ounces; |
| Dimensions: | ¾" depth, 4" width, and 12" length. |

Alternatively, the face material of the shearling comfort liner may be formed of 100% polyester. In other embodiments, the comfort liner may not include any shearling.

A heel elevating device is described above. Various details of the invention may be changed without departing from its scope. Furthermore, the foregoing description of the preferred embodiment of the invention and the best mode for practicing the invention are provided for the purpose of illustration only and not for the purpose of limitation-the invention being defined by the claims.

I claim:

1. A heel elevating device for being applied to the lower leg of a reclined patient to elevate the heel of the patient above a supporting surface, said heel elevating device comprising:
   (a) a generally U-shaped lower leg receiving support formed of a semi-rigid, resilient foam for supporting the lower leg of the patient therein on an interior surface thereof, and having a front, back, top and bottom, and depth extending from the front thereof to the back thereof, and a height extending from the bottom thereof to the top thereof the depth of said lower leg receiving support being less than one-half the height of said lower leg receiving support;
   (b) a comfort liner secured to the interior surface of said lower leg receiving support for cushioning the lower leg supported thereon and providing a soft, protective surface against the skin of the patient, said comfort liner comprising:
      (i) a cushion member overlying the interior surface of said lower leg support;
      (ii) a relatively thick fabric layer covering a top surface of said cushion member and defining a soft, skin-protective barrier adapted for residing between the skin of the patient and the cushion member, whereby said lower leg receiving support, cushion member, and fabric layer cooperate to form a three-stage progressively conformable support assembly acting against a relatively small area of the lower leg; and
   (c) adjustable fitting means for adjustably fitting the lower leg support to the lower leg of the patient.

2. A heel elevating device according to claim 1, wherein said lower leg support comprises a base and first and second spaced-apart extensions formed with said base, and wherein said adjustable fitting means includes an adjustable top strap adapted for extending over a top of the extensions and for adjustably spacing the extensions to snugly embrace the lower leg, said top strap having a connecting end attached to the first extension of said lower leg support, and a free end for being removably attached to the second extension of said lower leg support.

3. A heel elevating device according to claim 2, wherein the free end of said top strap and the second extension of said lower leg support include complementary hook and loop attachment members for removably attaching the top strap to the second extension.

4. A heel elevating device according to claim 2, wherein an inside surface of said top strap includes shearling for providing a soft, protective surface against the skin of the patient.

5. A heel elevating device according to claim 2, wherein said adjustable fitting means includes an adjustable foot-drop strap adapted for extending around the bottom of the foot to raise and maintain the foot in a 90° position, said foot-drop strap having a connecting end attached to the first extension of said lower leg support, and a free end for being removably attached to the second extension of said lower leg support.

6. A heel elevating device according to claim 5, wherein an inside surface of said foot-drop strap includes shearling for providing a soft, protective surface against the skin of the patient.

7. A heel elevating device according to claim 2, wherein a bottom surface of said comfort liner and a top surface of the base of said lower leg support include respective complementary hook and loop attachment members for removably attaching said comfort liner to the base of said lower leg support.

8. A heel elevating device according to claim 2, wherein a bottom surface of said comfort liner and an inside surface of each of the first and second extensions of said lower leg support include respective complementary hook and loop attachment members for removably attaching said comfort liner to the first and second extensions of said lower leg support.

9. A heel elevating device according to claim 2, wherein the base and first and second extensions of said lower leg support are integrally-formed.

10. A heel elevating device according to claim 2, wherein the base of said lower leg support has a smooth bottom surface for allowing sliding movement of the lower leg support over the supporting surface.

11. A heel elevating device according to claim 2, wherein the base of said lower leg support has a textured bottom surface for restricting sliding movement of the lower leg support over the supporting surface.

12. A heel elevating device according to claim 2, wherein the base of said lower leg support has a flat bottom surface for maintaining the foot in stationary position.

13. A heel elevating device according to claim 2, wherein the base of said lower leg support includes a rounded bottom surface for allowing limited side to side movement of the foot.

14. A heel elevating device according to claim 2, wherein the first and second extensions of said lower leg support have generally flat, respective outer surfaces.

15. A heel elevating device according to claim 1, wherein said relatively thick fabric layer of said comfort liner comprises shearling.

16. A heel elevating device according to claim 1, wherein said comfort liner includes a gel-filled thermal bladder.

17. A heel elevating device according to claim 1, wherein said comfort liner includes a foam cushion insert.

18. A heel elevating device according to claim 1, wherein said comfort liner includes an air bladder.

* * * * *